United States Patent
Kamei et al.

(10) Patent No.: US 8,008,614 B2
(45) Date of Patent: Aug. 30, 2011

(54) DEVICE FOR DETECTING EMISSION LIGHT OF MICRO-OBJECT HAVING MEANS FOR SUPPRESSING REFLECTED AND SCATTERED EXCITATION LIGHT

(75) Inventors: Toshihiro Kamei, Tsukuba (JP); Amane Shikanai, Tsukuba (JP); Akira Takahashi, Hanamaki (JP); Shigeyuki Furuta, Tokyo (JP)

(73) Assignees: National Institute of Advanced Industrial Science and Technology, Tokyo (JP); Ricoh Optical Industries Co., Ltd., Hanamaki-shi (JP)

( * ) Notice: Subject to any disclaimer, the term of this patent is extended or adjusted under 35 U.S.C. 154(b) by 287 days.

(21) Appl. No.: 12/486,504

(22) Filed: Jun. 17, 2009

(65) Prior Publication Data

US 2010/0038522 A1 Feb. 18, 2010

(30) Foreign Application Priority Data

Jun. 17, 2008 (JP) .................................. 2008-158162

(51) Int. Cl.
*G01J 3/50* (2006.01)
(52) U.S. Cl. ................................... 250/226; 250/237 R
(58) Field of Classification Search .................. 250/226, 250/216, 239, 201.3, 574, 205, 237 R, 458.1, 250/459.1, 492.1, 461.1; 356/436, 440, 246
See application file for complete search history.

(56) References Cited

U.S. PATENT DOCUMENTS

| 7,489,401 B2 | 2/2009 | Kamei et al. |
| 7,595,881 B2 * | 9/2009 | Leonard et al. ............... 356/436 |

FOREIGN PATENT DOCUMENTS

| JP | 2005-535871 | 11/2005 |
| JP | 2008-39655 | 2/2008 |
| WO | WO 03/102554 A1 | 12/2003 |

OTHER PUBLICATIONS

Toshihiro Kamei, et al., "Integrated Hydrogenated Amorphous Si Photodiode Detector for Microfluidic Bioanalytical Devices", Analytical Chemistry, vol. 75, No. 20, Oct. 15, 2003, pp. 5300-5305.
Toshihiro Kamei, et al., "Contact-lens type of micromachined hydrogenated amorphous Si fluorescence detector coupled with microfluidic electrophoresis devices", Applied Physics Letters 89, 2006, pp. 114101-1-114101-3.

* cited by examiner

*Primary Examiner* — Que T Le
(74) *Attorney, Agent, or Firm* — Oblon, Spivak, McClelland, Maier & Neustadt, L.L.P.

(57) ABSTRACT

The object of the present invention is to provide a device for detecting with higher sensitivity emission light in the form of fluorescence or phosphorescence emitted from a micro-object irradiated by an excitation light. The present invention provides means for suppressing reflected and scattered light arising from excitation light impinging on the semiconductor detection element of the device, comprising a pinhole formed in a fluorescence collecting microlens, through which the excitation light passes, irradiating the micro-object. The device may also be provided with another means for suppressing reflected and scattered excitation light comprising a non-horizontal surface that is not perpendicular to the excitation light, formed on a part of the light-transparent chip surface from which the excitation light exits.

4 Claims, 4 Drawing Sheets

DEVICE FOR DETECTING EMISSION LIGHT OF MICRO-OBJECT HAVING MEANS FOR SUPPRESSING REFLECTED AND SCATTERED EXCITATION LIGHT

TECHNICAL FIELD

This invention relates to a device for detecting with high sensitivity emission light emitted in the form of fluorescence or phosphorescence from a micro-object irradiated by an excitation light, and more particularly relates to a device incorporated into a microfluidic electrophoresis chip, microarray or other such microchip type analyzer for detecting with improved sensitivity the emission light of a micro-object such as when the micro-object is a fluorophore in biochemical analysis, a semiconductor quantum dot, or a micro-sample labeled with a fluorophore or a semiconductor quantum dot.

BACKGROUND ART

Electrophoresis is an analytic technique used in various biochemical analyses relating to nucleic acids such as DNA and RNA, amino acids and proteins and the like. Recently devices have been proposed that are capable of analyzing fluorescence emitted from a small amount of a solution sample in the order of nanoliters to picoliters by labeling the solution sample with an appropriate fluorophore when the sample is irradiated in a compact electrophoresis chip with an excitation light. The present inventors have also provided to date such devices and methods, which are disclosed in Patent document 1 and Non-Patent literature 1 by listed below.

FIGS. 4 (A) and (B) illustrate an example of a previous device disclosed by the present inventors in the Patent document 1 and Non-Patent literature 1. With reference to the drawings, the device has a chip 10 for containing and supporting an analytical sample. The chip 10 is provided with mutually planar intersecting microchannels 15 and 16. One of these, channel 15 called an injection channel, is provided at one end thereof with a well-shaped sample reservoir 11 for containing a sample in the form of a solution, and at the other end thereof with a waste reservoir 12 for receiving the sample flowing out via the injection channel 15. The other channel 16 which intersects the injection channel 15, called a separation channel, is provided at one end thereof with a cathode reservoir 13 and at the other end thereof with an anode reservoir 14. The reservoirs 11 to 14 are each provided with electrodes (not shown) in the form such as a thin-film electrode, for example, or inserted electrodes that are needle-shaped or the like, for the purpose of applying individually preset voltages at the timings described below. The channels 15 and 16 generally intersect each other orthogonally, as illustrated, forming the shape of a cross in a plan view.

When a sample is loaded into the sample reservoir 11 and an appropriate voltage is applied between the sample reservoir 11 and the waste reservoir 12, the sample migrates into the injection channel 15. At this time, the cathode reservoir 13 and the anode reservoir 14 are kept in a floating potential state or an appropriate bias voltage is applied therebetween. When the voltage is switched after the lapse of an appropriate time (generally in the order of 10 to 60 seconds) and an appropriate voltage is applied between the cathode reservoir 13 and the anode reservoir 14, a portion of the sample (called the sample plug) that has just reached the point of intersection with the separation channel 16 is excised, and electrophoresis begins inside the separation channel 16. Further, at this time, an appropriate bias voltage is applied between the sample reservoir 11 and the waste reservoir 12 so that the residual sample that remains in the injection channel 15 does not flow into the separation channel 16.

By utilizing recent semiconductor microfabrication technology, it is possible to form the channels 15 and 16 to a very fine width with good accuracy, and therefore form a short sample plug corresponding to the channel width (generally some tens of micrometers). In practice, the chip 10 is usually manufactured by bonding two glass sheets together, since it is required to have the highest possible optical transmittance in the wavelength of at least the excitation light or fluorescence and to have a good insulating property to the electrophoresis. The channels 15 and 16 are lithographically (in some cases, mechanically) formed on one glass sheet 10a, and subsequently thermal bonding is used to affix the other glass sheet 10b which occludes the channels 15 and 16 from above and which is perforated with vertical holes to form the reservoirs 11-14. It is also possible to use plastic substrates. The two plate members are bonded together by using thermal bonding, ultrasonic welding, or an adhesive agent. It should be noted that this invention does not impose any particular restriction on the structure of this part. It only needs to have a structure suitable for analysis; a conventional configuration may of course be used.

Thus, even with existing fabrication technology, an extremely short sample plug can be obtained, so electrophoretic separation with a high number of theoretical plates can be achieved by using a microfluidic electrophoresis chip having a short channel length. As mentioned above, the sample migrating inside the separation channel 16 is labeled in advance with an appropriate fluorophore. When it is irradiated with an excitation light Le, it therefore emits a light of a different wavelength from the excitation light, generally fluorescence. When the labeled sample plug is migrating inside the separation channel 16, the sample plug reaches to the detection region Po while being separated according to differences in the size of the sample plug and the electric charge and so forth. A so-called electropherogram (electrophoresis data) can be obtained by plotting the intensity of the fluorescence emitted as a result of being irradiated in the detection region Po with the excitation light Le against the time required for the sample plug to reach the detection region Po.

FIG. 4 (B) shows a conventional-construction fluorescence detecting module 40 for detecting the fluorescence. The fluorescence detecting module 40 has a semiconductor light detecting element 20, which in the illustrated cross section appears to be a lateral pair of elements. In fact, as can be seen in a plan view, it is a doughnut-shaped element with a center pinhole 41 through which the excitation light Le passes to irradiate the sample. When this excitation light Le impinges on the chip 10 transparent to the light and irradiates the sample in the separation channel 16 inside the detection region Po, the sample emits fluorescence Lf. Then, the fluorescence Lf is transformed by a microlens 61 for collecting the fluorescence preferably into nearly parallel rays and enters an optical filter 50 disposed on the incidence plane side of the semiconductor light detecting element 20. The optical filter 50 is generally configured as an optical interference filter formed by coating one surface side of a quartz glass 52, and is able to selectively transmit the fluorescence Lf in order to remove as much of the scattered excitation light Le as possible and allow just the fluorescence Lf to fall incident onto the semiconductor light detecting element 20. The fluorescence collecting microlens 61 may be formed integrally with the chip 10 by cast molding or may be formed on a special base plate 61', as partially depicted in FIG. 4 (B) by an imaginary line, and bonded to the rear surface of the chip 10.

The specific structure of the optical interference filter 50 or the semiconductor light detecting element 20 may be an existing structure, as described below with reference to the embodiments of the invention. That is, modifying the basic structure of the members 50 and 20 is not an object of the invention. As described in the Patent Document 1 and Non-patent Document 1, the semiconductor light detecting element 20 used for the detecting device of the invention preferably comprises a photodiode fabricated using hydrogenated amorphous silicon (a-Si:H).

That is because a-Si:H photodiode has various desirable characteristics, not only in the case of the electrophoresis method but also in the case of biochemical analysis, as listed below.

1) A fluorescence band of fluorophores (such as, for example, Fluorescein, Green Fluorescence Protein, TOTO, and Ethidium Bromide) is located in a visible light region, in which a-Si:H has a high absorption coefficient with respect to visible light.

2) A dark current of a-Si:H is several orders of magnitude lower than that of crystalline silicon, so an a-Si:H photodiode does not require cooling, which is advantageous with respect to decreasing device size.

3) A-Si:H can be patterned by using semiconductor microfabrication technology, facilitating the fabrication of photodiode detector arrays.

4) A-Si:H photodiodes have good mass-producibility and can be formed directly on cheap glass or plastic substrates by using plasma enhanced chemical vapor deposition, facilitating low-cost implementation.

The present inventors actually fabricated an integrated a-Si:H photodiode as disclosed in the Non-document 1 mentioned and tested it using an argon ion laser (excitation wavelength $\lambda=488$ nm) as an excitation light source. When the fabricated photodiode was evaluated by detecting fluorescence from a fluorescein fluorophore, the limit of detection was found to be 17 nanomole/L (hereinafter abbreviated as "nM") for fluorescein concentration. As disclosed in Non-Patent literature 2 listed below, the inventors also fabricated a fluorescence detecting element in which the optical interference filter was integrated monolithically on the a-Si:H photodiode, and tested the element using a solid-state laser (excitation wavelength $\lambda=488$ nm) as the excitation light source. The result showed that the detection limit was further decreased, to a fluorescein concentration of 7 nM. Based on those results, the device showed the highest detection sensitivity among the several examples of fluorescence detector of this sort reported to date. This device was in fact successfully applied to the analysis of microfluidic DNA fragments and enantiomers of amino acids. As further variations, Patent document 2, listed below, discloses using a micro-resonator type light-emitting diode (LED) as an excitation light source, and adapting as an excitation light source an LED having an emission aperture no wider than a micro-object.

The final target to be attained by these fluorescence detecting devices is the realization of a so-called lab-on-a-chip or micro total analysis system (μTAS). That is, the target is to integrate and miniaturize, on a single chip, all the elements necessary for a series of analytic processes or analysis, enabling "point-of-care" analysis. To some extent the concepts of the method of fluorescence detection analysis were indeed established prior to the disclosures of Patent documents 1 and 2 and Non-Patents literature 1 and 2. Actually, in the case of microfluidic electrophoresis, high-speed genotyping using 96 to 384 channels was in fact carried out. Moreover, microfluidic valves and pumps were proposed and made available for enabling large-scale parallel microfluidic operations, making it possible to perform microfluidic cell sorting and combinatorial optimization for protein crystallization conditions in large-scale integrated microchambers.

Analytical processes such as electrophoresis and sample preparation processes have become successfully integrated and miniaturized and enabled partially to undergo large-scale integration. However, in most cases, a laser-induced fluorescence detection system composed of a photomultiplier, a CCD, an optical interference filter, and a laser is used for microfluidic lab-on-a-chip analysis, due to the need for high-sensitivity detection of microsamples. Such a system can hardly be called a readily portable device suitable for "point-of-care" analysis. In this respect, the aforementioned system proposed by the present inventors has built a foundation for realizing "point-of-care" biochemical analysis with high speed and low sample consumption. When this success is further developed to the point of the construction and practical realization of a lab-on-a-chip, the lab-on-a-chip will be useful enough for the prompt detection and identification of pathogens scattered by so-called bioterrorism, diagnosing genetic diseases, and performing stress monitoring and the like, and therefore can be expected to have a huge industrial impact.

Patent document 1: JP2005-535871 (B)
Patent document 2: JP2008-039655 (A)
Non-Patent literature 1: T. Kamei et al., "Integrated Hydrogenated Amorphous Si Photodiode Detector for Microfluidic Bioanalytical Devices," Anal. Chem., Vol. 75, No. 20(Oct. 15, 2003), pp.5300-5305.
Non-Patent literature 2: T. Kamei et al., "Contact-lens type of micromachined hydrogenated amorphous Si fluorescence detector coupled with microfluidic electrophoresis devices", Appl. Phys. Lett., Vol. 89, pp. 114101-1-3 (2006)

DISCLOSURE OF THE INVENTION

Problems which the Invention Tries to Solve

For this, the effect of reflection and scattering of the excitation light has to be considered. Clearly, it is necessary to adequately remove excitation light reflected and scattered as it passes through the lens, optical filter and other optical components and the light-transparent chip 10 (a microfluidic electrophoresis chip or micro-array or the like) on which the sample is supported. Herein, reflected or scattered excitation light or reflected light and scattered light will be referred to as "reflected and scattered light". This problem was something that was not much of a concern with a conventional laser induced fluorescence detection system since, in such a system, there was complete separation between the excitation light source and the detecting element and two optical filters were used, a emission filter and a dichroic beam-splitter. As a result, the reflected and scattered laser light had little effect, on detecting fluorescence, which was rarely hindered. In addition, because the confocal optical system used a spatial filter such as pinhole, it was possible to more completely eliminate reflected and scattered laser light.

In the case of an integrated fluorescence detection system that enables point-of-care analysis, which is the aim of the present inventors, the reflected and scattered light becomes a major problem. For example, in the case of detecting the fluorescence of a fluoroscein fluorophore having a concentration of 1 nM, with the structure of FIG. 4 (B), although the light scattered at the interface between the fluorescence collecting microlens 61 and the light-transparent chip 10 may be weak compared to the intensity of the original excitation light, it has a major effect on the fluorescence detection sensitivity. That is because the number of excitation light photons is ten orders of magnitude larger than the number of fluorescence photons. If optical interference filter 50 is unable to remove all of the scattered light produced at that interface, it impinges on the semiconductor light-detecting element 20 and is observed as background photocurrent. The main cause of detection noise is noise components superposed on this background photocurrent, limiting the limit of detection.

One reason that can be cited for the inability of the optical interference filter 50 to filter out all the scattered light is that even if the filter can act on the light falling vertically incident on the filter surface, it cannot fully filter out scattered light falling at an oblique angle. Because it is difficult to predict all the angles of the incident scattered light, there is a limit to how much can be removed by just only the use of the optical interference filter 50. Especially when the wavelengths of the excitation light and fluorescence are close, the characteristics of the filter 50 are prone to angle dependency, making it difficult to separate out the scattered light by using just only the filter 50. Therefore in order to raise the detection sensitivity and decrease the limit of detection of an integrated fluorescence detection system, the integrated optical system needs specialized technology that can greatly suppress reflected and scattered light from the excitation light. The main object of this invention is to resolve that problem.

Means for Solving the Problem

To attain the above object, the present inventors propose an improved micro-object emission light detecting device in which light emitted in the form of fluorescence or phosphorescence from a micro-object supported on a light-transparent chip that is subjected to irradiation by excitation light from an excitation light source is converged by a fluorescence collecting microlens and detected by impinging on a semiconductor light-detecting element, and which is also provided with means for suppressing reflected and scattered light arising from the excitation light impinging on the semiconductor light-detecting element.

In accordance with a first aspect of the invention, the means for suppressing reflected and scattered excitation light includes an excitation light transmission pinhole formed in the fluorescence collecting microlens so that the micro-object is irradiated by the excitation light passing through the transmission pinhole. The pinhole may be a mechanical through-hole, or a blind hole that is transparent to the excitation light.

In accordance with a second aspect of the invention, the means for suppressing reflected and scattered excitation light has a non-horizontal surface that is not perpendicular to the excitation light, formed on a part of an exit surface of the light-transparent chip from which excitation light transmitted exits, and that inclines reflected light produced by the excitation light being reflected by the non-horizontal surface.

In accordance with a third aspect of the invention, the means for suppressing reflected and scattered excitation light includes an antireflection film provided on the part of the fluorescence collecting microlens on which the excitation light falls incident. In accordance with a fourth aspect, the means for suppressing reflected and scattered excitation light includes an excitation light absorbing material or an excitation light antireflection film provided on a part of an exit surface from which excitation light transmitted from the light-transparent chip exits.

The above means for suppressing reflected and scattered excitation light described in each of the first to fourth aspects may be used independently, or in combination for more effectiveness.

Effects of the Invention

In accordance with the present invention, a very effective means for suppressing reflected and scattered excitation light is disclosed that, compared to conventional devices, provides much greater suppression of reflected and scattered light arising from excitation light at the interface between the light-transparent chip and the fluorescence collecting microlens, with no sacrifice in productivity. Detection noise is caused mainly by noise components superposed on background photocurrent caused by reflected and scattered light, so the noise components can be greatly reduced by reducing the background photocurrent. As a result, limit of detection values can be lowered, and in combination with polymerase chain reactions (PCR), the invention can be applied to even more advanced biochemical analysis, such as single molecular nucleic acid detection and DNA sequencing and the like.

Employing the above-described structural principle, and also because the present invention can be implemented at a much lower cost, the present invention is not limited to analysis electrophoresis, but can be applied to a wide range of bioanalysis. The present invention is capable of providing an extremely effective means for realizing all types of microfluidic lab-on-a-chip based on fluorescence detection, and can also be applied to fluorescence detection systems such as DNA microarrays and protein microarrays. It could be applicable to DNA fragment sizing analysis, protein separation, amino acid analysis, cell sorting and drug screening. Moreover, the present invention can be used for point-of-care detection and identification of pathogens when combined with a device that integrates and couples PCR and electrophoresis.

Particularly when a semiconductor quantum dot is used instead of a fluorophore as in DNA microarray analysis in which the large mass thereof is not much of a hindrance, the present invention can be effectively used in fluorescence detection.

BRIEF DESCRIPTION OF THE DRAWINGS

FIG. 4 (B) is a longitudinal sectional view of the conventional device disclosed by the inventors in Patent Document 1 and Non-patent Document 1.

BEST MODE FOR CARRYING OUT THE INVENTION

Figure 1:
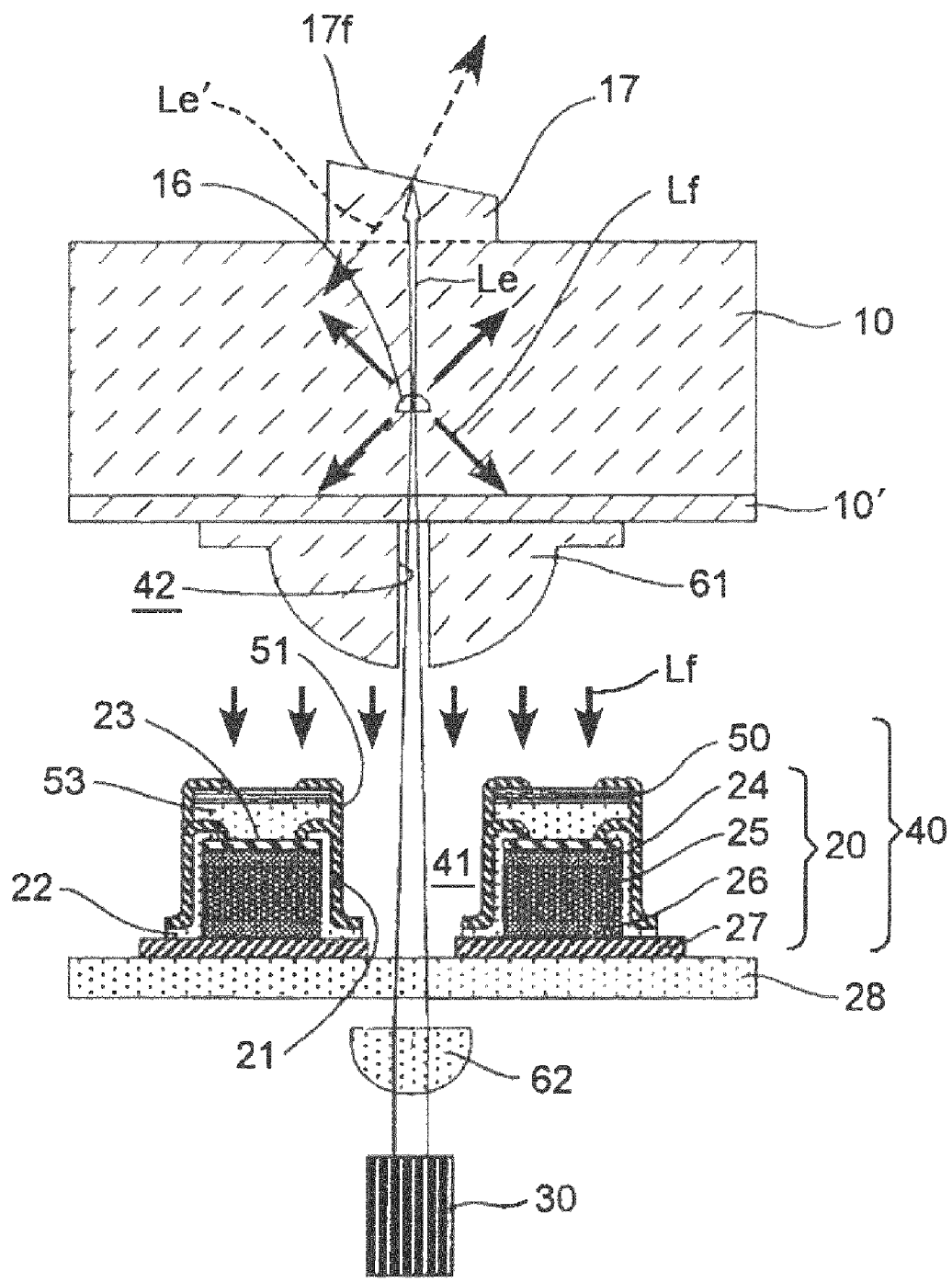
FIG. 1 is a longitudinal sectional view of a fluorescence detecting device according to a first embodiment of the present invention.
Figure 4A:
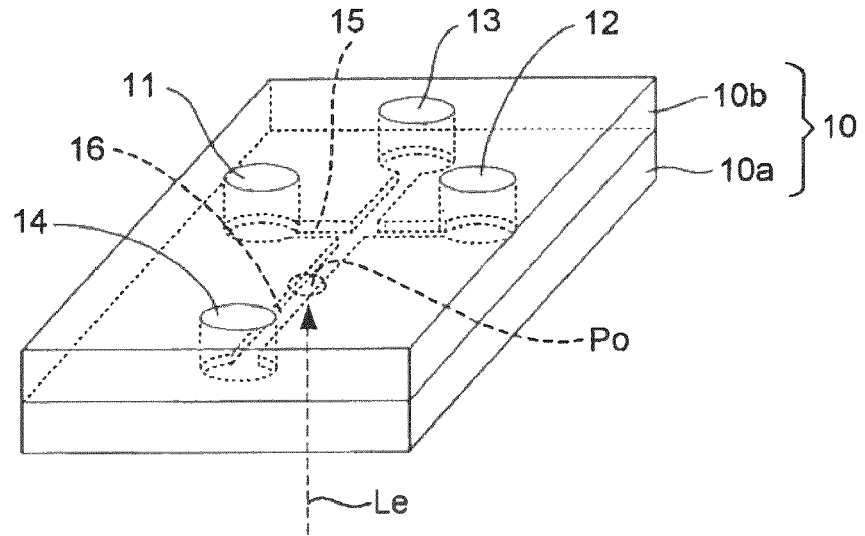
FIG. 4 (A) is a perspective view of a light-transparent chip 10 used in a conventional device disclosed by the inventors in Patent Document 1 and Non-patent Document 1.
Figure 4B:
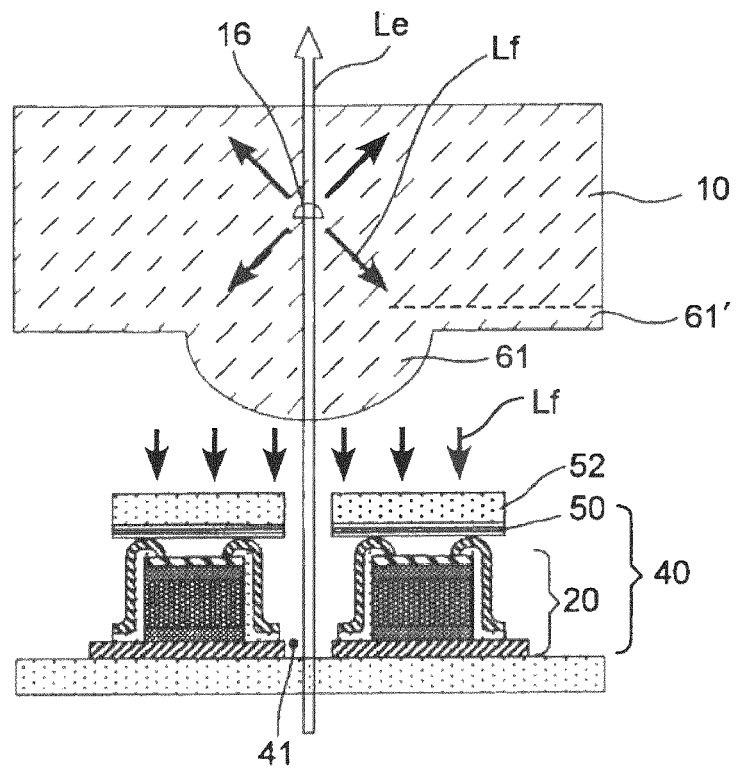

FIG. 1 illustrates a preferred embodiment of this invention. As regards the reference numerals affixed to the component elements of the conventional example already described with reference to FIGS. 4 (A) and 4 (B) and the reference numerals used in the other diagrams, identical reference numerals denote identical or similar component elements. Concerning the component elements, the contents already explained somewhere, are applicable elsewhere, and unless otherwise specified, repeated explanation thereof may be omitted.

First Embodiment

The embodiment of this invention shown in FIG. 1 is configured based on the assumption it is to be applied to the electrophoretic analysis already described. The micro-object which generates fluorescence in this case as emission light resulting from irradiation with an exciting light Le, therefore, is a sample plug (not illustrated) labeled with a fluorophore and passing through a separation channel 16 in a light-transparent chip 10 composed of glass or plastic substrate, as already described.

An excitation light transmission pinhole 42 is formed in the center of a fluorescence collecting microlens 61 provided on the light-transparent chip 10 via a light-transparent spacer 10' in this embodiment and this pinhole 42 forms a means for suppressing reflection and scattering of excitation light Le. The excitation light Le emitted by an excitation light source 30 comprised of a semiconductor laser diode or the like is collected by an excitation light collecting microlens 62 and passes through the pinhole 42 in the fluorescence collecting microlens 61, irradiating the separation channel 16.

This embodiment is provided with another reflected and scattered light suppression means, disposed on the surface of the light-transparent chip 10 from which the excitation light exits. Specifically, with reference to FIG. 1, a non-horizontal surface member 17 having a wedge-shaped cross-section that is formed of a light-transparent substrate or the like is provided on the top of the light-transparent chip 10 from which the excitation light Le exits. The non-horizontal surface member 17 has a non-horizontal surface 17f that is not perpendicular to the excitation light Le. Therefore, when excitation light Le transmitted by the separation channel 16 exits into the air from the non-horizontal surface 17f, reflected light Le' that is reflected into the light-transparent chip 10 propagates obliquely. Here, 'non-horizontal' means not perpendicular to the excitation light Le, and does not relate to the temporal geometrical attitude of the device.

This could also be expressed as saying that the non-horizontal surface 17f only needs to be non-perpendicular with respect to the excitation light Le, so that as shown in FIG. 1, it may be a surface set at an oblique angle to the excitation light exit surface of the light-transparent chip 10, or a surface having an indeterminate shape, or a curved surface. Therefore, the non-horizontal surface member 17 that bears the non-horizontal surface 17f is not limited to being a wedge-shaped substrate, but may be a prism or a plano-convex lens or the like. It may be formed of any material able to adequately transmit the excitation light Le, such as glass and plastic.

Fluorescence Lf emitted due to the irradiation of the excitation light Le is made parallel by the fluorescence collecting microlens 61 and detected by fluorescence detecting module 40. A pinhole 41 for transmitting the excitation light Le is formed preferably in the center of the fluorescence detecting module 40, a part in which fluorescence cannot be detected. That can actually be advantageous, since even though in accordance with the invention an excitation light transmission pinhole 42 is formed in the middle of the fluorescence collecting microlens 61, it does not affect fluorescence detection.

Preferably, the semiconductor light-detecting element 20 of the fluorescence detecting module 40 is an a-Si:H photodiode 20 which is composed of a-Si:H material. Generally, an a-Si:H film can be fabricated using a low-temperature process at 200° C. to 300° C., so it can be formed directly on an inexpensive substrate such as glass or plastic. The illustrated embodiment assumes such a case. With this invention, however, it is not necessary to specify the structure of the a-Si:H photodiode 20 itself, which may be composed by the use of a known structure. Here, for reference, the process of fabricating the photodiode shown in FIG. 1 will be described briefly.

A bottom electrode 27 is formed by sputtering an appropriate conductive material such as chromium on a transparent substrate 28, for example, glass substrate 28. The sequential deposition of an N type a-Si:H film 26, an intrinsic a-Si:H film 25, and a P-type a-Si:H film 24 thereon is followed by the deposition of a top transparent conductive electrode 23, using for example ITO. The patterning of the a-Si photodiode 20 including an electrode is done at a suitable time by photolithography so as to make the photodiode doughnut-shaped with the pinhole 41 at its center. In the above-mentioned structure, the pinhole 41 in the bottom electrode 27 acts as an aperture for the excitation light Le.

The side wall of the photodiode 20 formed as a PIN type as described above is covered with an appropriate insulating film 22 such as SiN, and is then covered with an appropriate metal film 21 such as aluminum. This metal film 21 is electrically connected to the top of transparent conductive film 23 to form the other electrode opposed to the bottom electrode. The deposition of an insulating film 53 such as SiO on this a-Si:H photodiode 20 is preferably followed by chemical mechanical polishing (CMP) or the like to flatten the surface, on which optical filter 50 is then formed. The optical filter 50 is ordinarily formed as an optical interference filter. The optical interference filter 50 is formed, for example, of $SiO_2$/$Ta_2O_5$ or the like. The fabrication of this optical interference filter which selectively transmits the fluorescence Lf and blocks the excitation light Le is well known and can be arbitrarily applied to this invention. Thus, the details thereof are omitted here.

Preferably, the side wall of the optical interference filter 50 is covered with a shielding film 51. The material of this insulating film 51 is arbitrary, being only required to block the excitation light to the fullest possible extent, and may be a coating film that blocks the light, or may even be a metal film; selecting aluminum, the same material used for the electrode of the photodiode 20, is convenient in terms of the fabrication process.

In the case of this embodiment, the structure that characterizes the present invention comprises the excitation light transmission pinhole 42 formed in the center of the fluorescence collecting microlens 61, and the non-horizontal surface portion 17f through which the excitation light Le transmitted by the light-transparent chip 10 exits. The above-mentioned components respectively form means for suppressing reflection and scattering of excitation light Le. Excitation light Le reflected and scattered towards the fluorescence detecting module 40 arises from the surface of the light-transparent chip 10 at the bottom of the excitation light transmission pinhole 42 (the surface of the light-transparent spacer 10' in the case of the illustrated embodiment). In the case of the conventional structure in which, unlike that of this invention, does not have a pinhole 42, the excitation light Le is reflected and scattered at the top of the fluorescence collecting microlens 61. As a result, in the structure of the present invention the distance from the point at which the reflected and scattered light of the excitation light Le exits on the side towards the fluorescence detecting module 40 to the fluorescence detecting module 40 is longer than in the case of the conventional structure having no pinhole 42. As a result, in the case of the present inventive structure the reflected and scattered light impinges on the optical filter 50 at an angle that is close to the perpendicular, enabling it to be filtered out more effectively. Forming the pinhole 42 also reduces the problem of autofluorescence from the fluorescence collecting microlens 61.

Providing the structure with the non-horizontal surface 17f reduces background photocurrent caused by scattered laser light by obliquely deflecting the reflected excitation light Le' produced at the surface of the light-transparent chip 10.

While the light-transparent spacer 10' is a member separate from the light-transparent chip 10 and the spacer 10' is assumed to be optically coupled with the light-transparent chip 10 by refractive index matching oil, the spacer 10' may be formed integrally with the chip. Similarly, the non-horizontal surface member 17 is a separate member from the light-transparent chip 10 to which it is coupled by a refractive index matching oil, but may be formed integrally with the chip.

Second Embodiment

Figure 2:
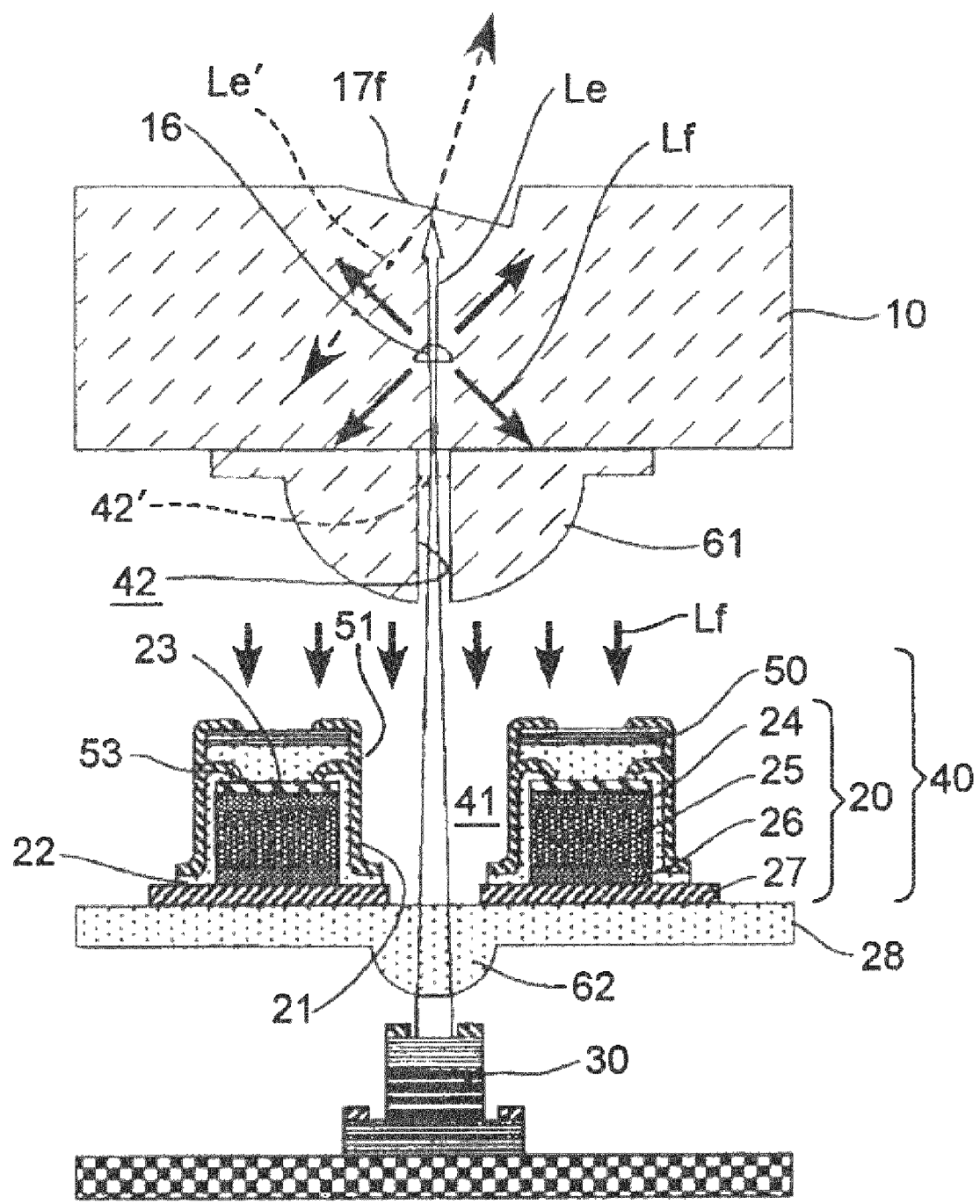
FIG. 2 is a longitudinal sectional view of a fluorescence detecting device according to a second embodiment of the present invention.

FIG. 2 shows a second embodiment of the invention. Elements not explained in the following are identical or similar to elements described with reference to FIG. 1. What is different is the structural portion that forms the non-horizontal surface 17f that is shaped so that the excitation light Le exits the light-transparent chip 10 non-perpendicularly. That is, the light-transparent chip 10 of the second embodiment uses the same members as the first embodiment and has the same internal structure, and the surface of the light-transparent chip 10 from which the excitation light Le exits is processed. This comprises the forming of an obliquely angled recessed portion in the surface of the light-transparent chip 10 to form the non-horizontal surface 17f. It has the same significance as in the first embodiment, which is to suppress reflection and scattering of the excitation light Le. Because the non-horizontal surface 17f in this second embodiment is formed as a recess in a parallel plane substrate, it has the advantage of being formable using semiconductor lithography using the exposure apparatus.

In this second embodiment, also, there is no light-transparent spacer 10', the fluorescence collecting microlens 61 being disposed directly on the light-transparent chip 10, which is a simpler structure than the first embodiment. Also, while in the first embodiment the pinhole 42 passes completely through the fluorescence collecting microlens 61, the pinhole 42 does not have to have the configuration similar to the one shown in FIG. 2. As shown by the imaginary line 42' in FIG. 2, if it is structured by using a material that is highly transparent enough to the excitation light Le to function substantially as a pinhole that provides the stated effect of the invention, it may be a blind hole.

In the second embodiment, also, when a plurality of separation channels 16 is used, a surface emitting laser can be used as the excitation light source 30, which is advantageous in terms of the manufacturing. Also convenient in this embodiment is that the excitation light collecting microlens 62 that converges the excitation light Le is constructed integrally on the substrate 28 of the fluorescence detecting module 40 at a location inside the pinhole 41.

Third Embodiment

Figure 3:
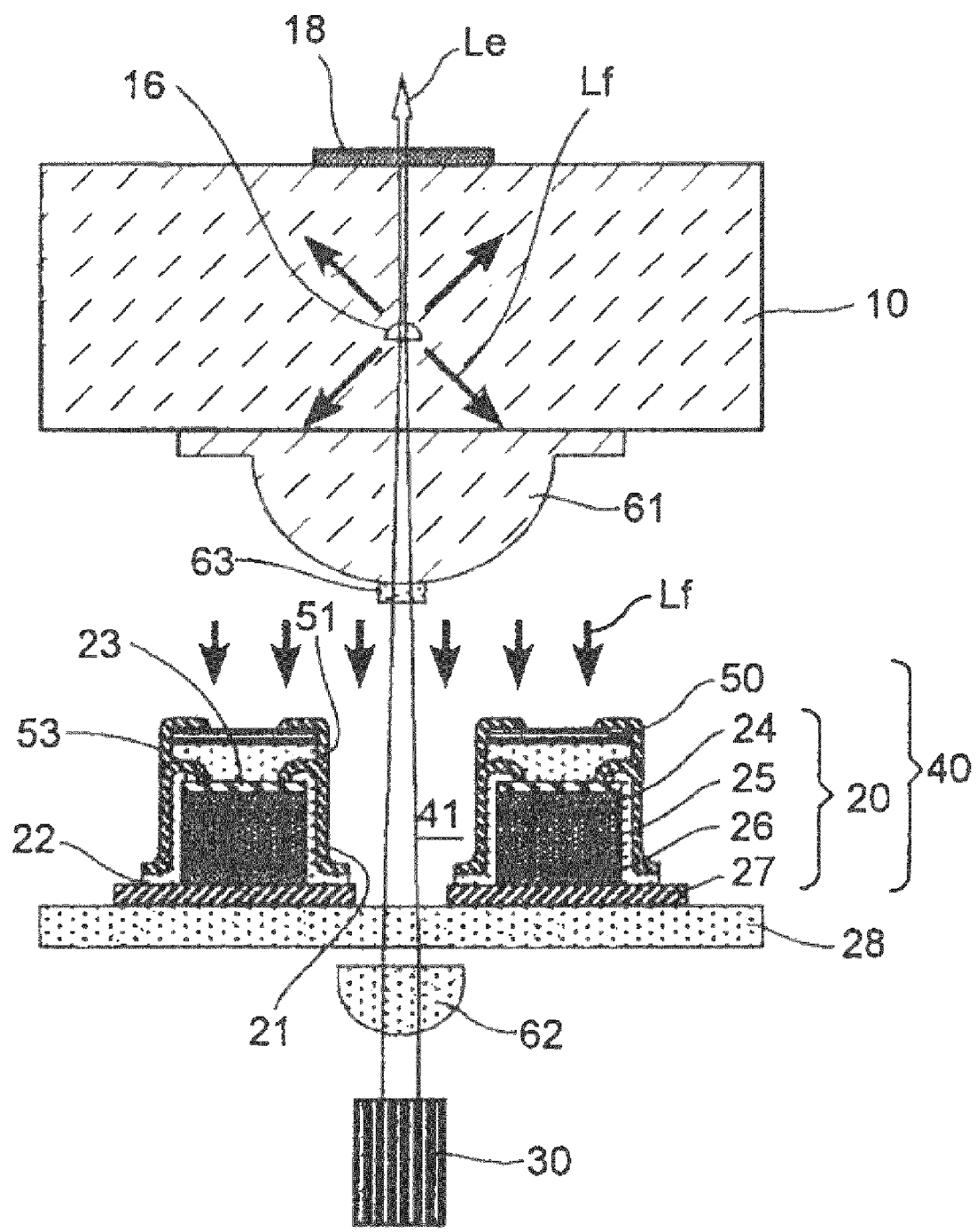
FIG. 3 is a longitudinal sectional view of a fluorescence detecting device according to a third embodiment of the present invention.

FIG. 3 shows a third embodiment. Again, the explanation used in the first and second embodiments applies to structural elements not described here. The means for suppressing reflection and scattering of the excitation light Le in this embodiment comprises an antireflection film 63 selectively provided at least at the top part of the fluorescence collecting microlens 61 at the part where the excitation light Le impinges. The antireflection film 63 is preferably a multilayer structure of $SiO_2/Ta_2O_5$ or the like which, as shown, may be selectively used on only the top part of the fluorescence collecting microlens 61 through which the excitation light Le passes. That is because the antireflection multilayer structure has an angle-of-incidence dependency that reduces the transmission of fluorescence around the periphery of the microlens 61.

Thus, in accordance with this invention, reflection and scattering of the excitation light Le can be effectively suppressed by the provision of the antireflection film 63 as the reflected and scattered light suppression means. The suppression means can be applied to the first and second embodiments by providing the antireflection film 63 on the excitation light Le incident surface. That is, in the case of the first embodiment the antireflection film would be provided on the lower surface of the spacer 10', which is to say, between the fluorescence collecting microlens 61 and the spacer 10'. In the case of the second embodiment, when there is an excitation light transmission pinhole formed in the microlens, the antireflection film 63 would be provided on the lower surface of the light-transparent chip 10, and in the case of a blind hole, it would be provided on the lower side of the blind hole. That is, the antireflection film 63 would be provided between the fluorescence collecting microlens 61 and the light-transparent chip 10. When the antireflection film is a single layer of $MgF_2$ or the like, the angle-of-incidence dependency is not very large and so the antireflection film 63 may be formed over the whole surface of the fluorescence collecting microlens 61, but in some cases there may be a problem of spontaneous luminescence from the $MgF_2$.

This third embodiment also has another reflected and scattered light suppression means in the form of an excitation light absorbing member 18 comprising a coating of black ink or the like applied to the portion of the surface of the light-transparent chip 10 from which the excitation light exits. By absorbing the excitation light Le, this portion serves to suppress light scattered and/or reflected at the upper surface of the light-transparent chip 10.

Instead of using a coating applied to form the excitation light absorbing member 18, black plastic or the like can be bonded to the excitation light exit portion. Also, in place of the excitation light absorbing member, an antireflection film having the same configuration as the antireflection film 63 used on the fluorescence collecting microlens 61 may be provided on the excitation light exit portion.

Each of the three embodiments of the present invention described in the foregoing uses an effective reflected and scattered light suppression means to markedly reduce background photocurrent caused by reflection and scattering of the excitation light Le. That reduces the noise component superposed on the background photocurrent, markedly improving the detection sensitivity and further lowering the limit of detection. As has been made clear, the means for suppressing reflected and scattered excitation light described with respect to each embodiment may each be used alone or as a combination of a plurality thereof.

While not a requirement of the invention, when the a-Si:H photodiode described above is used as the semiconductor light-detecting element 20, it is usual to apply a reverse bias in the order of several volts to the a-Si:H photodiode 20 to optimize the carrier collection efficiency.

The shape of the fluorescence detecting module 40 is not limited to that of a doughnut, and only needs to be formed in a solid shape that surrounds the through hole. For example, it can be formed as a quadrilateral or other polygonal shape as seen in a plan view, with a through hole 41 of a circular shape or a polygonal shape with n vertices opened in a part thereof (generally at the center) for the excitation light Le to pass through.

Various examples of other modifications are possible. For example, the semiconductor light-detecting element 20 may be comprised of a plurality of a-Si:H photodiodes, which respectively have an optical filter having a different spectral characteristic so as to enable multiplex analysis of the wavelengths of the fluorescence. Analysis such as DNA sequencing can be realized by labeling adenine, guanine, thymine, and cytosine with fluorophores that fluoresce at different wavelengths. As mentioned in the foregoing, even when the emission light is fluorescence from a semiconductor quantum dot or fluorescence from micro-object labeled with the semiconductor quantum dot, the present invention can be advantageously applied to detecting the fluorescence as emission light. It is also clear that the present invention can be suitable applied to the detection of phosphorescence as well as fluorescence.

The semiconductor light-detecting element of the present invention may be composed of a so-called photoconductor instead of the photodiode described in the above. Elements that use such photoconductors are very well known, so incorporating photoconductors in place of the above-described semiconductor light-emitting element would not be difficult for a person skilled in the art. If a photodiode is used, it is preferably formed of a-Si:H, as described. But it is not limited to that material. Materials available to compose the photodiode used in the present invention include alloys such as, for example, hydrogenated amorphous silicon-germanium alloys and hydrogenated amorphous silicon-carbide alloys which are readily fabricated by the same method simply by changing the source gas. Compared to a-Si:H, these alloys each have higher sensitivity to long- and short-wavelength light, respectively. The invention can also use photodiodes composed of microcrystalline silicon and alloy materials thereof which can be readily fabricated by the same method simply by changing the conditions of deposition such as the ratio of hydrogen dilution. Thus, modifications may be arbitrarily used to the extent that they do not depart from the gist of the invention.

What is claimed is:

1. A micro-object emission light detecting device comprising:
    an excitation light source that emits excitation light;
    a light-transparent chip that supports a micro-object labeled with a fluorophore;
    a fluorescence collecting microlens that converges fluorescence or phosphorescence emitted by the micro-object irradiated by the excitation light;
    a semiconductor light-detecting element on which the converged emitted light falls incident; and
    means for suppressing reflected and scattered light arising from excitation light falling incident on the semiconductor light-emitting element,
    the means for suppressing reflected and scattered excitation light including an excitation light transmission pinhole formed in the fluorescence collecting microlens, wherein
    the excitation light passes through said pinhole and irradiates the micro-object.

2. A micro-object emission light detecting device comprising:
    an excitation light source that emits excitation light;
    a light-transparent chip that supports a micro-object labeled with a fluorophore;
    a fluorescence collecting microlens that converges fluorescence or phosphorescence emitted by the micro-object irradiated by the excitation light;
    a semiconductor light-detecting element on which the converged emitted light falls incident; and
    means for suppressing reflected and scattered light arising from excitation light falling incident on the semiconductor light-emitting element,
    the means for suppressing reflected and scattered excitation light comprising a non-horizontal surface which is not perpendicular to the excitation light, and which is formed on a part of the light-transparent chip where transmitted excitation light exits, and which inclines reflected light of the excitation light reflected at the non-horizontal surface.

3. A micro-object emission light detecting device comprising:
    an excitation light source that emits excitation light;
    a light-transparent chip that supports a micro-object labeled with a fluorophore;
    a fluorescence collecting microlens that converges fluorescence or phosphorescence emitted by the micro-object irradiated by the excitation light;
    a semiconductor light-detecting element on which the converged emitted light falls incident; and
    means for suppressing reflected and scattered light arising from excitation light falling incident on the semiconductor light-emitting element,
    the means for suppressing reflected and scattered excitation light including an antireflection film provided on a part of the fluorescence collecting microlens on which excitation light falls incident.

4. A micro-object emission light detecting device comprising:
    an excitation light source that emits excitation light;
    a light-transparent chip that supports a micro-object labeled with a fluorophore;
    a fluorescence collecting microlens that converges fluorescence or phosphorescence emitted by the micro-object irradiated by the excitation light;
    a semiconductor light-detecting element on which the converged emitted light falls incident; and
    means for suppressing reflected and scattered light arising from excitation light falling incident on the semiconductor light-emitting element,
    the means for suppressing reflected and scattered excitation light including an excitation light absorbing member or an excitation light antireflection film provided on a part of an exit surface from which excitation light transmitted from the light-transparent chip exits.

* * * * *